United States Patent [19]

Gangemi

[11] Patent Number: 5,040,699
[45] Date of Patent: Aug. 20, 1991

[54] FLUID COMPOUNDING METHOD AND APPARATUS

[76] Inventor: Ronald J. Gangemi, 10607 Banner Mine Way, Nevada City, Calif. 95959

[21] Appl. No.: 351,719

[22] Filed: May 15, 1989

[51] Int. Cl.⁵ .................................................. B65B 3/28
[52] U.S. Cl. .......................................... 222/1; 222/58; 222/59; 141/104; 141/105
[58] Field of Search ...................... 366/141; 222/1, 14, 222/23, 39, 52, 58-59, 63, 77, 132, 135, 138, 145, 142, 144.5, 185, 255; 141/83, 94, 100, 103, 104, 105; 137/567, 889

[56] References Cited

U.S. PATENT DOCUMENTS

| | | | |
|---|---|---|---|
| 3,749,285 | 7/1973 | Latham, Jr. | 222/58 |
| 4,512,764 | 4/1985 | Wunsch | 604/80 |
| 4,513,796 | 4/1985 | Miller et al. | 141/83 |
| 4,648,430 | 3/1987 | Di Gianfilippo et al. | 141/1 |
| 4,718,467 | 1/1988 | Di Gionfilippo et al. | 141/105 |
| 4,789,014 | 12/1988 | Di Gianfilippo et al. | 222/77 X |

Primary Examiner—Michael S. Huppert
Attorney, Agent, or Firm—John G. Mesaros

[57] ABSTRACT

A fluid compounding method and apparatus including a plurality of peristaltic pumps, the tubing for which, on one end, is connected to individual solution dispensing containers, with the other end being coupled through a manifold to an admixed solution receiving container. Each fluid dispensing station is provided with a load cell, each of which individually monitors the weight of the dispensing solution container. Electronic logic circuitry, including a microprocessor and program in read only memory, it utilized and accessed by an operator via a keyboard, into which the operator enters the desired volume and the specific gravity of each of the solutions being dispensed. The circuitry then converts each of these inputs to a weight factor against which the weight of the receiving container is monitored. To commence operation, the weight of each dispensing container is measured and stored, that is, the load cell for each dispensing station senses the weight of the dispensing container and solution. All pumps are then actuated simultaneously, with the weight of the dispensing container at each station being continuously monitored. The first pump to stop will be the pump for the dispensing solution which requires the least weight or volume, with the other pumps then stoppings, in turn, until the pump which is dispensing the greatest volume finally stops. With all pumps being actuated simultaneously, the total fluid compounding time is significantly reduced.

26 Claims, 9 Drawing Sheets

FLUID COMPOUNDING METHOD AND APPARATUS

BACKGROUND OF THE INVENTION

The background of the invention will be discussed in two parts.

FIELD OF THE INVENTION

This invention relates to a fluid compounding method and apparatus, and more particularly to a fluid compound method and apparatus for simultaneously dispensing two or more solutions into a compounding container.

DESCRIPTION OF THE PRIOR ART

Fluid compounding of solutions, such as parenteral, enteral or pharmaceutical solutions is usually performed on a volumetric basis, that is, the solutions to be mixed are mixed in accordance with percent by volume. Such solutions, individually may have different specific gravities, sometimes within a small percentage of one another, and the specific gravity must be taken into consideration when compounding the admixed solution in order to obtain the proper volumetric ratios.

Prior art fluid compounding apparatus, such as shown and described in U.S. Pat. No. 4,513,796, issued to Miller et al on Apr. 30, 1985, employs a plurality of peristaltic pumps, the tubing for which, on one end, is connected to individual solution dispensing containers, with the other end being coupled through a manifold to an admixed solution receiving container which is suspended from a load cell. Electronic logic circuitry is utilized and accessed by an operator via a keyboard. In the prior art device, three pumping stations are provided, with three stations for receiving three solution dispensing containers. The operator, via the keyboard, enters the desired volume and the specific gravity of each of the solutions being dispensed. The circuitry then converts each of these inputs to a weight factor against which the weight of the receiving container is monitored.

To commence operation, with the empty receiving container suspended from the load cell, the first pump is then energized to pump a first predetermined weight of solution into the receiving container, which weight is sensed by the load cell and correlated against the weight computed by the circuitry for the first dispensing solution. After the cessation of pumping of the first pump, the second pump is energized until the additional weight of the receiving container is equal to the weight value determined for the second solution. After the cessation of the second pump, the third pump is started, and after the appropriate weight of solution is dispensed, the pump is stopped, with the result being the total amount of admixed solution desired in the receiving container.

With such prior art devices, the total compounding time is additive, that is, the total time required for admixing the solution in the receiving container is the total time for each of the four sequential pumping cycles.

In accordance with an aspect of the inventions, it is an object of the present invention to provide a new and improved fluid compounding apparatus in which the fluid compounding time for admixing two or more solutions is determined by the maximum time required for dispensing one solution.

SUMMARY OF THE INVENTION

The foregoing and other objects of the invention are accomplished by providing fluid compounding apparatus including a plurality of peristaltic pumps, the tubing for which, on one end, is connected to individual solution dispensing supply containers, with the other end being coupled through a manifold to an admixed solution receiving container. Each fluid dispensing station is provided with a weight measuring means, such as a load cell, each of which individually monitors the weight of the dispensing solution container. Electronic logic circuitry, including a microprocessor and program in read only memory, is utilized and accessed by an operator via a keyboard on a control panel.

The operator, by use of the keyboard, enters the desired volume and the specific gravity of each of the solutions being dispensed. The circuitry then converts each of these inputs to a weight factor against which the weight of the receiving container is monitored. To commence operation, the weight of each supply container is measured and stored, that is, the load cell for each dispensing station-senses the weight of the dispensing container and solution.

All pumps are then actuated simultaneously, with the weight of the dispensing container at each station being continuously monitored. The first pump to stop will be the pump for the dispensing solution which requires the least weight or volume, with the other pumps then stopping, in turn, until the pump which is dispensing the greatest volume finally stops. With all pumps being actuated simultaneously, the total fluid compounding time is significantly reduced.

Other objects, features and advantages of the invention will become apparent from a reading of the specification when taken in conjunction with the drawings.

DESCRIPTION OF THE PREFERRED EMBODIMENTS

Description of the Apparatus

Figure 1:
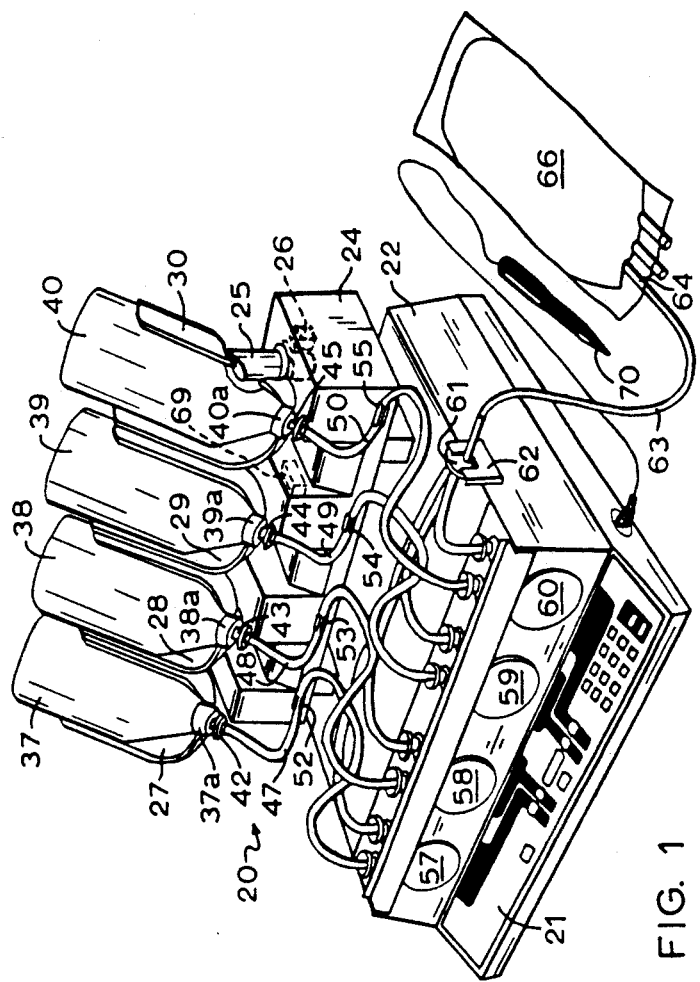
FIG. 1 is a perspective view, partially exploded and partially broken away, of the fluid compounding apparatus according to the invention.

Referring now to the drawings, and particularly to FIG. 1, there is shown a fluid compounding apparatus, generally designated 20, which includes a base housing 22 configured for receiving therein the electronic components, with the bottom of the housing 22 configured for resting on a supporting surface. The front portion of the housing 22 is configured to form a control panel 21, in connection with which the operator enters appropriate values for the solution desired as will hereinafter be explained.

Attached to the rear of the upper part of the base housing 22 is a dispensing or supply container subhousing 24 configured as a box-like enclosure. The subhousing 24 is configured with contoured openings (not shown) for receiving therein a plurality of generally cylindrically cradle support members 25, each being configured with a tapered upper edge, each of the members 25 being inserted into the opening with the axis thereof in a generally vertical position, that is, perpendicular to the surface supporting the base housing 22. The taper of the upper edge of each member 25 is configured for attachment thereto of a cradle, such as cradles 27-30, each of which is of a contoured open or shell-shaped configuration for receiving therein one of a plurality of solution dispensing supply containers 37-40 with the neck or dispensing ends 37a-40a of the containers pointing downwardly. Within the subhousing 24, the cradle support members rest on and physically coact, via support members 25, with a corresponding weight sensing means, such as load cells 26 (only one of which is shown), the load cells 26 providing an electrical output signal proportional to the weight sensed thereby.

Figure 3:
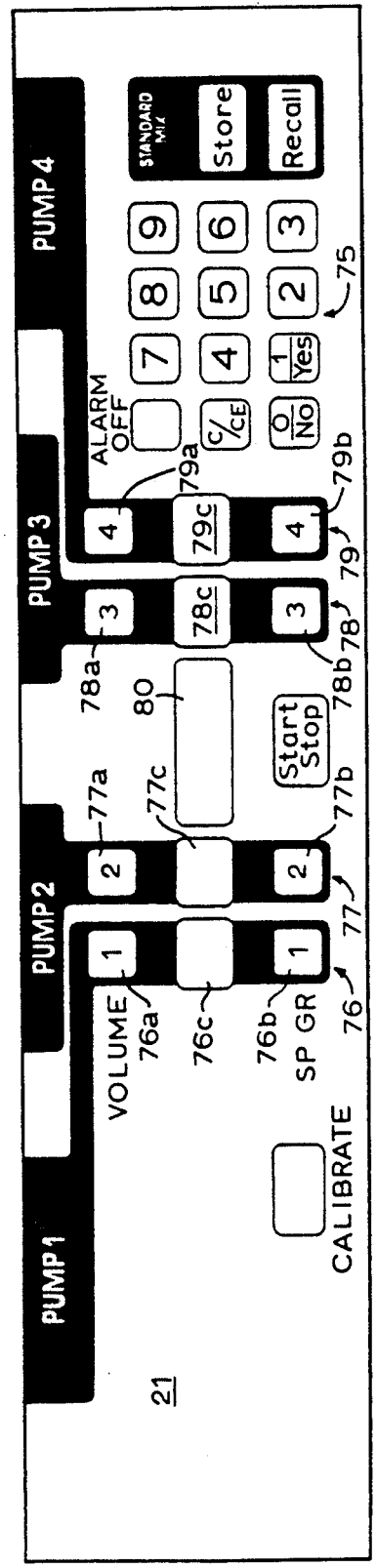
FIG. 3 is a plan view of the keyboard control panel of the apparatus of FIG. 1.

Each dispensing end 37a-40a of the supply containers 37-40 has inserted therein an air evacuating dispenser fitting 42-45 with lengths of flexible surgical plastic tubing 47-50 having one end connected thereto. The tubing 47-50 is secured at the end adjacent thereto by clip members 52-55 which are suitably attached to the adjacent surface of the subhousing 24. The lengths of tubing 47-50 are then threaded about the reels 51 (only one of which is shown in FIG. 3) of peristaltic pumping devices 57-60. Peristaltic pumping devices are well known in the art and provide a method of sterile pumping by use of the cross members of the rotating reels 51 urging against stationary sections of the tubing to permit movement of the solution through the tubing without the pump coming in contact with the solution.

The lengths of tubing 47-50 pass from the fittings 42-45 partially encircling the reels 51 with the other ends of the tubing 47-50 then being coupled to a four input manifold 61 which has a single outlet fitting to which is connected one end of a length of tubing 63, the other end of which is connected to a fitting 64 coupled to the open end of a sterile plastic bag or solution receiving container 66. The manifold 61 is maintained in a stationary position by insertion within a manifold support member 62 which is affixed adjacent a corner of the housing 22.

It is to be noted, for reasons which will become apparent hereinafter, that, with the manifold 61 positioned at one side of the housing 22, the individual lengths of the tubing 47-50 are different, that is, the tubing 47 for dispensing container 37 (the most removed from manifold 61), is longer than the tubing 50 (the most proximate to the manifold 61). As a consequence, when accuracy is desired, the fluid contained within the varying length of tubing must be taken into consideration. In other words, with the load cells 26 measuring the weight of each of the combined solution and dispensing containers 37-40, on priming, a small quantity of fluid from the containers 37-40 is dispensed into the lengths of tubing 47-50, prior to discharge into the receiving container 66, and this amount of fluid must be taken into consideration for accuracy in the final volume. Furthermore due to the varying lengths of the tubing, the volume dispensed from each container 37-40 will vary according to the length of the tubing.

Figure 2:
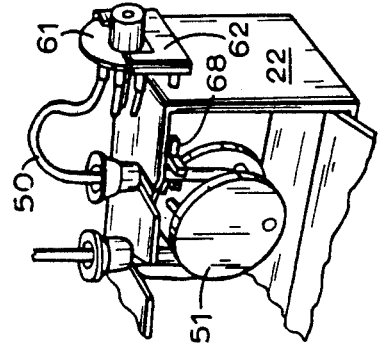
FIG. 2 is a perspective view of a corner of the apparatus of FIG. 1 showing details of the fluid dispensing sensor.

As will be hereinafter described, the pumping devices 57-60 are actuated to simultaneously pump fluid or solution from the dispensing containers 37-70 through the tubing 47-50 through the manifold 61 and ultimately into the receiving container 66. In order to provide an indication that fluid is flowing through the lengths of tubing 47-50, each pumping station is provided with appropriate fluid flow sensing means, such as an optoelectronic infra-red sensor 68, only one of which is shown in FIG. 2, the sensor 68 being commonly referred to as a "bubble detector", which has a pair of spaced arms through which the discharge ends of the tubing 47-50 pass in proximity to the reel 51. The tubing 47-50 is generally transparent, and the transparency of the tubing varies with a fluid within the tubing section between the arms of the sensor 68. This varying degree of transparency is sensed by the sensor 68 and when the transparency sensed is that of the tubing alone, an alarm sounds for operator attention. The basic principal of operation of the sensors 68 is that liquid has a different refraction index than air. As a result, there is a difference in detector output level between air and liquid in the tubing 47-50.

Since electrical weight measuring devices, such as load cells 26, are sensitive to variations in temperature, in order to provide accurate results, a temperature measuring device, such as temperature sensor 69 (shown in dotted lines in FIG. 1) is positioned within the subhousing 24 at a position wherein the ambient temperature within the enclosure of subhousing 24 may be constantly monitored to enable the electronics to determine if electrical compensation should be made to account for temperature fluctuations. The temperature sensor 69 is mounted in proximity to the load cells 26. The output of the sensor 69 is utilized on initial calibration of the system, and thereafter on power up as well as electrical adjustment of the system after each cycle when temperature variations beyond a preset norm are sensed.

In contrast to the prior art apparatus in which the supply containers are suspended, in the instant invention, the subhousing 24 is configured for positioning the supply containers 37-40 in a broad based shell-like cradle 27-30 which is configured for support of the major portion of the supply container with the dispensing ends 37a-40a of the supply containers 37-40 in proximate relation to the upper surface of the base housing 22. In fluid compounding apparatus, with the pumping devices 57-60 actuated, vibration is a common problem. In order to minimize the effect of the vibration on the load cells 26, the apparatus 20 is configured in a compact manner with the cradles 27-30 in close proximity to the load cells within the housing 22.

A bar code wand 70 is electrically connected to the system, the wand 70 being utilized in conjunction with a bar code (not shown) imprinted on the receiving bag or container 66. In fluid compounding for pharmaceutical or hospital usage, sterility is required. In accordance with the apparatus 20, the supply containers 37-40 are sterile, as is the tubing 47-50 and the manifold 61. Peristaltic pumps 57-60 are used to insure sterility. To further promote a sterile environment, each receiving bag or container 66 is provided with a unique bar code identification to prevent reuse. By utilization of the bar code wand, the identification of each container 66 is recorded in memory. When the bar code wand is used, and a previously stored identification number is read, an alarm sound and a message appears in the display 80 of the control panel 21. If the bar code thus read is a unique number not previously used, the reading of the bar code may be utilized to initiate pumping action.

In accordance with the invention, by reference to FIG. 3, there is shown the control panel 21, which includes a keyboard having a ten digit data entry numeric keypad portion 75, through which the operator enters numeric values, four solution value entry or pump station control portions 76-79, a liquid crystal display 80 and various other control switches 82-85. The display 80 displays alphanumeric characters and serves to display messages as well as numbers entered through the keypad 75.

Each of the pump station control portions 76-79 includes a select button 76a-79a for enabling volume entry, that is, the volumes of solution desired to be dispensed for the particular selected pumping station; a select button 76b-79b for enabling specific gravity entry, that is the specific gravity for the solution desired to be dispensed for the particular selected pumping station; and a small display 76c-79c for display of the value so entered.

The fundamental theory of operation of the apparatus of FIG. 1 is as follows, the operator enters the volume of the solution required from each supply or dispensing container 37-40 (two or more) and the specific gravity of each solution by station. The operator attaches the appropriate size receiving container 6 and scans the bar code label with the bar code wand 70 to insure that a previously used bag or receiving container is not being reused (to insure sterility). The system accepts the information on the bar code label and starts pumping all requested solutions simultaneously. The amount of solution being pumped is monitored by the supply container load cells 26. Once the correct volume is pumped, the system stops, alerts the operator, and waits for the next cycle.

Brief Description of the System Block Diagram

Figure 4:
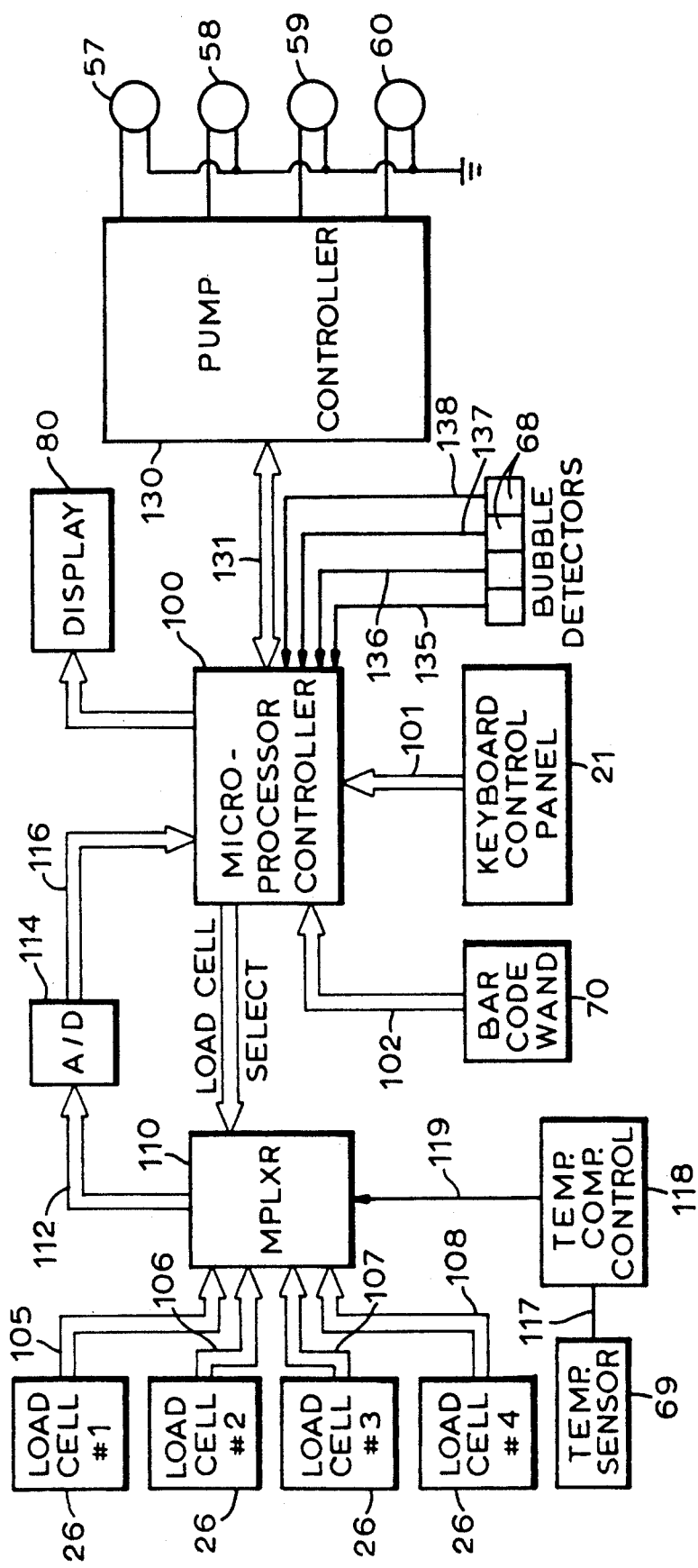
FIG. 4 is a block diagram of the electronic circuitry utilized in the apparatus of FIG. 1.

FIG. 4 depicts a block diagram of the electronic portion of the fluid compounding apparatus 20. In this block diagram, components or devices corresponding to those shown or described in connection with FIGS. 1 through 3 bear corresponding reference numerals. Briefly, the electronic portion includes a microprocessor controller 100 which communicates with the keyboard control panel 21 and bar code wand 70 via lines or buses 101 and 102, respectively. Information is output from the controller 100 to the display 80 (which may also include the specific gravity/volume displays 76c-79c).

Four load cells 26 (designated load cell #1, load cell #2, etc.) have the outputs thereof transmitted over lines 105-108, respectively, to provide inputs to a multiplexer 110. The outputs from the load cells 26 are analog outputs which are sequentially sampled and multiplexed over lines 112 to an analog to digital converter 114, the digital output of which passes over lines 116 to the controller 100. Another signal from the temperature sensor 69 is transmitted through the multiplexer ∠, via output line 117, through temperature compensation controller 118 over line 119 to the multiplexer 110. Multiplexer control and selection ar accomplished by the controller 100 over lines 120, designated "load cell select", it being understood that these lines also control temperature compensation selection, as required.

For pump actuation, a pump controller 130 communicates with the microprocessor controller 100 via bus 131, with the output of pump controller 130 selectively energizing each of the pumping devices 57-59. The remaining control signals from the four bubble detectors or sensors 68 (shown in ganged relation although they are physically separate), are transmitted to the controller 100 via lines 135-138.

In general, the system, under control of the microprocessor controller 100, receives initial values for solution dispensing from the keyboard control panel 21 (and, if desired, the bar code wand 70); monitors condition sensitive signals, i.e., load cell 26 signals and flow sensor 68 signals; and, under control of the program, transmits signals to the pump controller 130 to control the individual pumping devices 57-59, to thereby provide the required volumetrically proportioned solution to the receiving container 66 from the constituent solutions in the supply containers 37-40.

Description of the Circuitry

Figure 5:
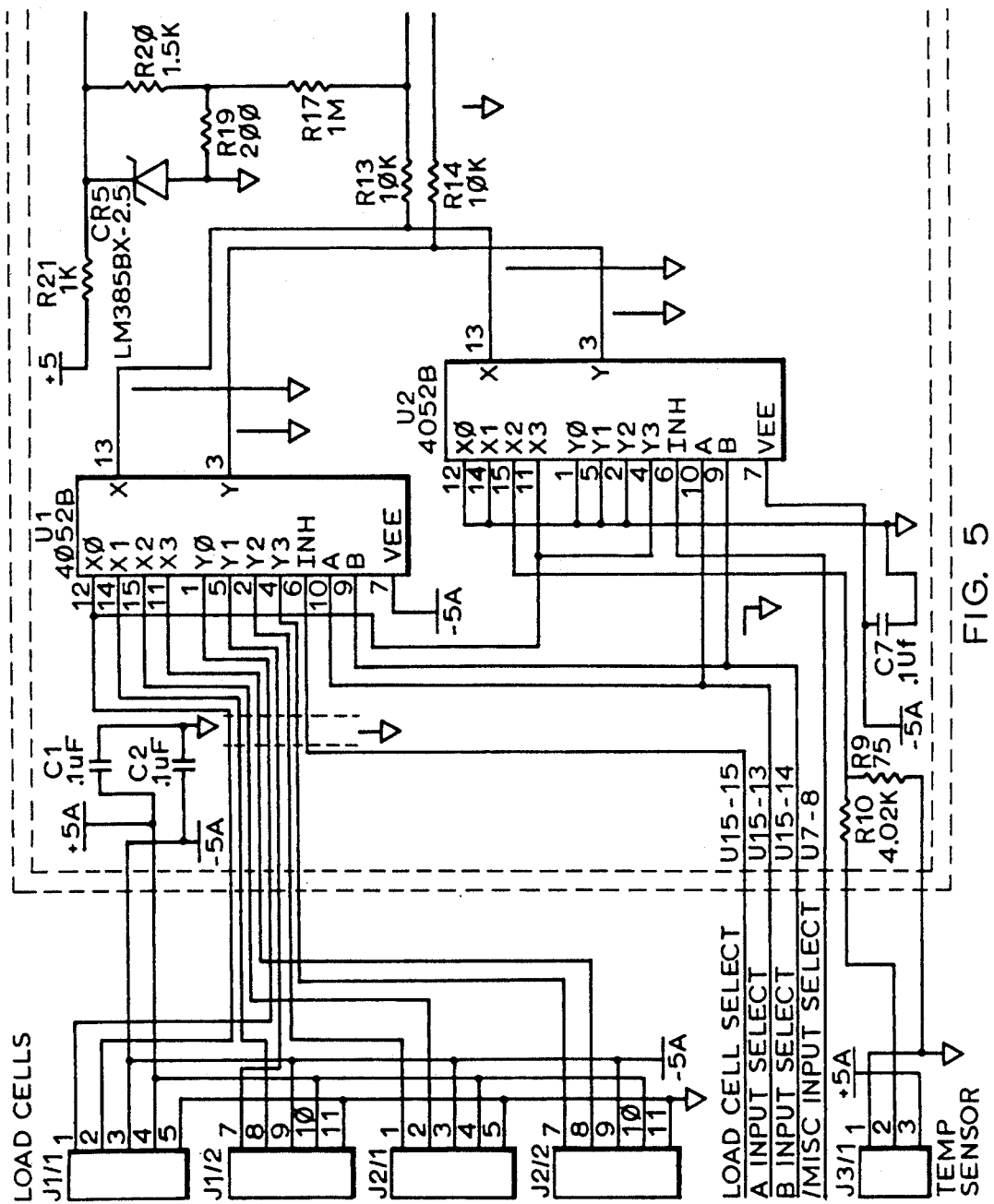
FIG. 5, consisting of two sheets of drawings labeled FIG. 5 and FIG. 5 CONT., are collectively referred to hereinafter as FIG. 5 which, with FIG. 5 and FIG. 5 CONT. laid side by side with FIG. 5 on the left, form a schematic diagram of a portion of the electronic circuitry of the fluid compounding apparatus of FIG. 1.
Figure 5:
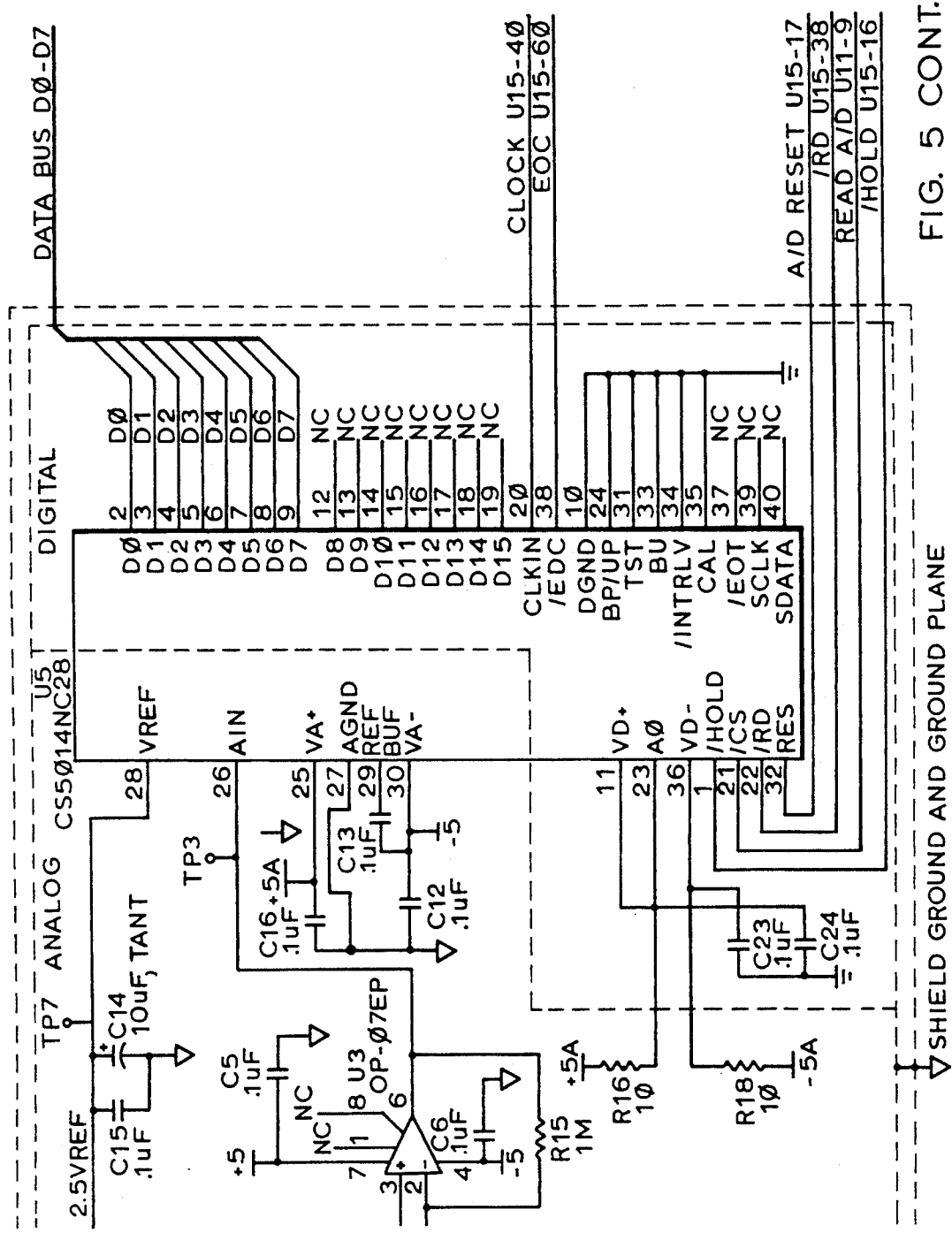
Figure 6A:
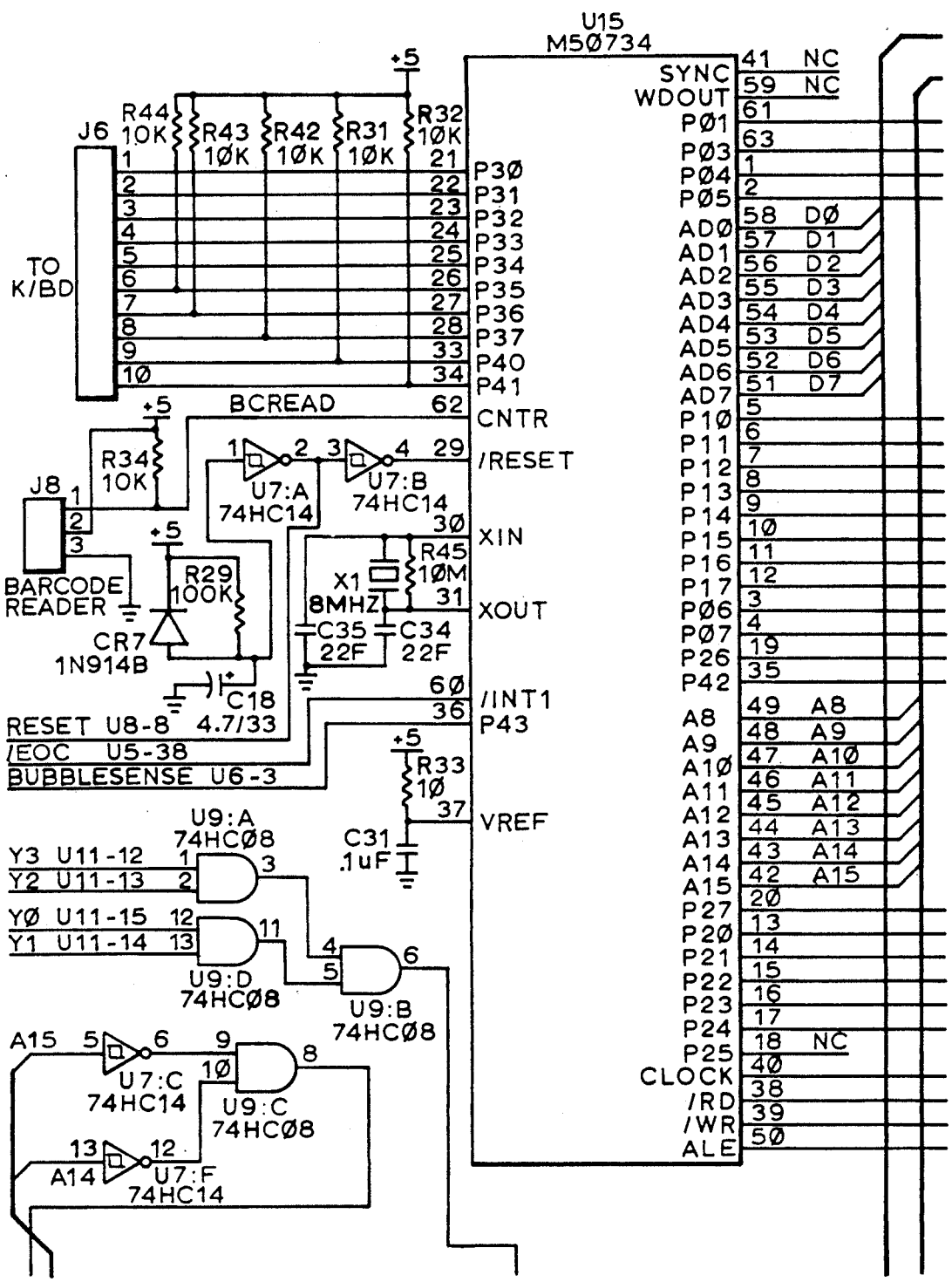
FIG. 6, consisting of four sheets of drawings labeled FIG. 6a, 6b, 6c and 6d, collectively referred to hereinafter as FIG. 6, which, with FIG. 6a and 6b laid side by side with FIG. 6a on the left, with FIG. 6c and 6d laid side by side with FIG. 6c on the left and both positioned beneath FIGS. 6a and 6b, form a schematic diagram of a portion of the electronic circuitry of the fluid compounding apparatus of FIG. 1.
Figure 6B:
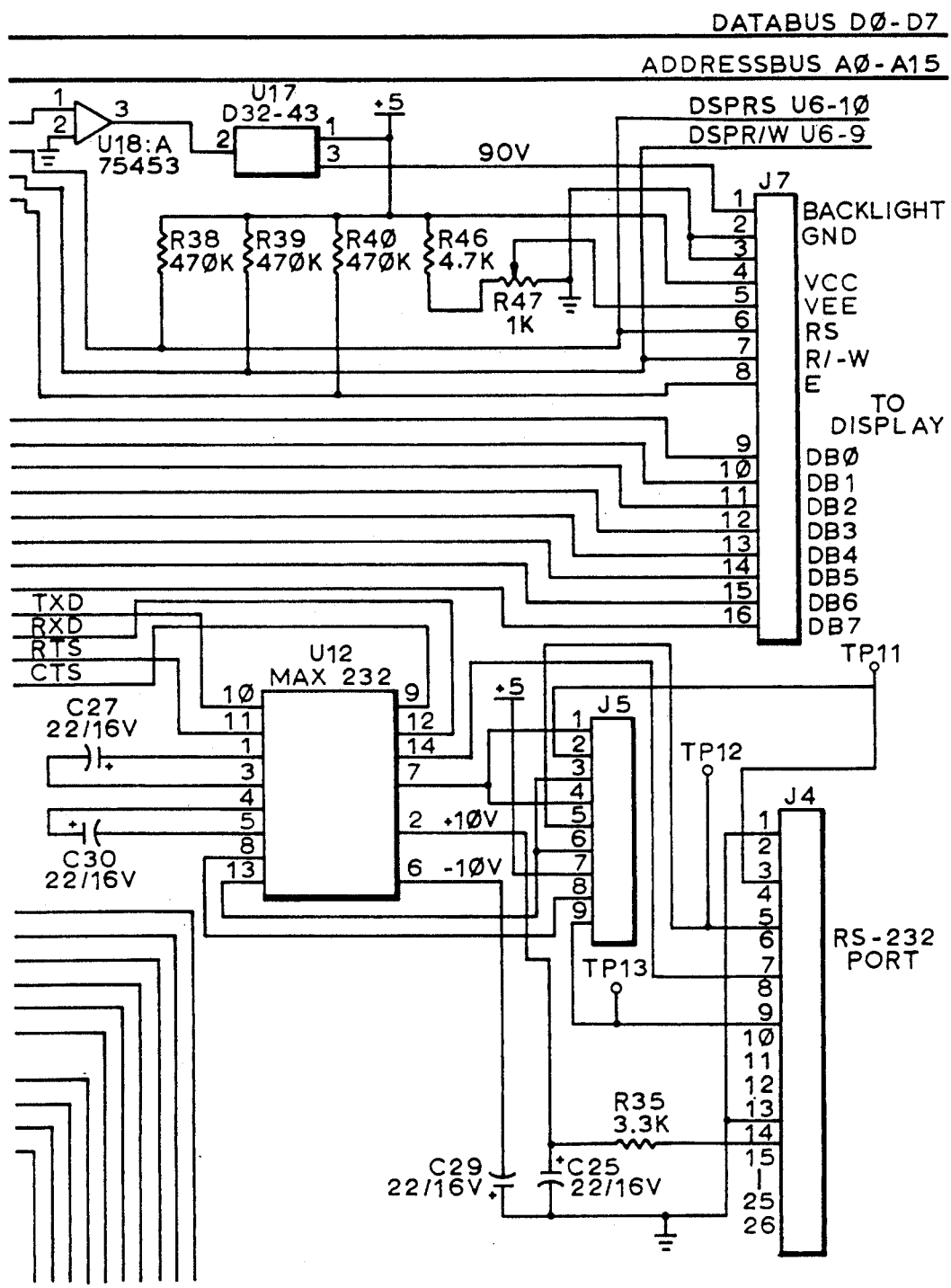
Figure 6C:
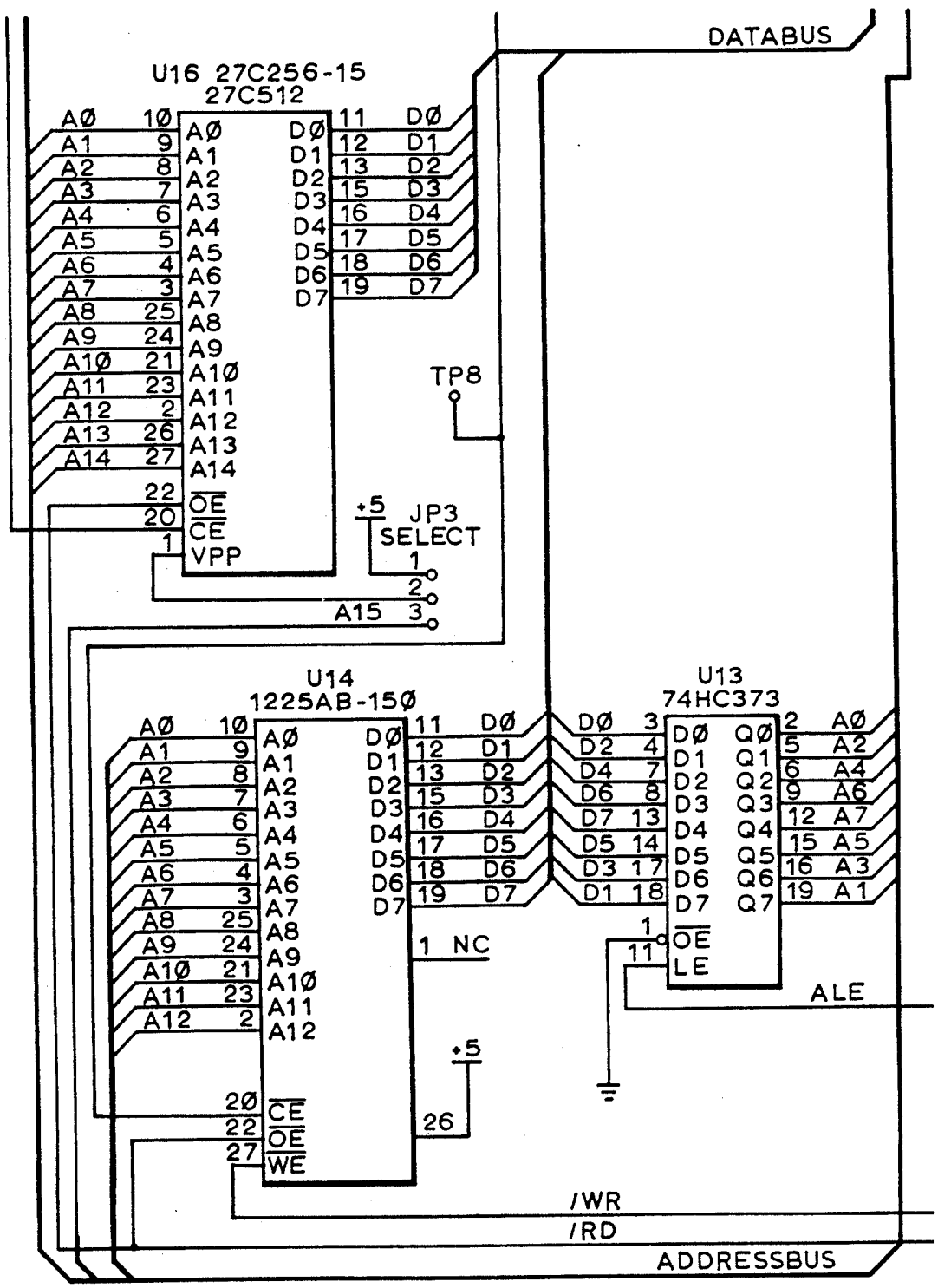
Figure 6D:
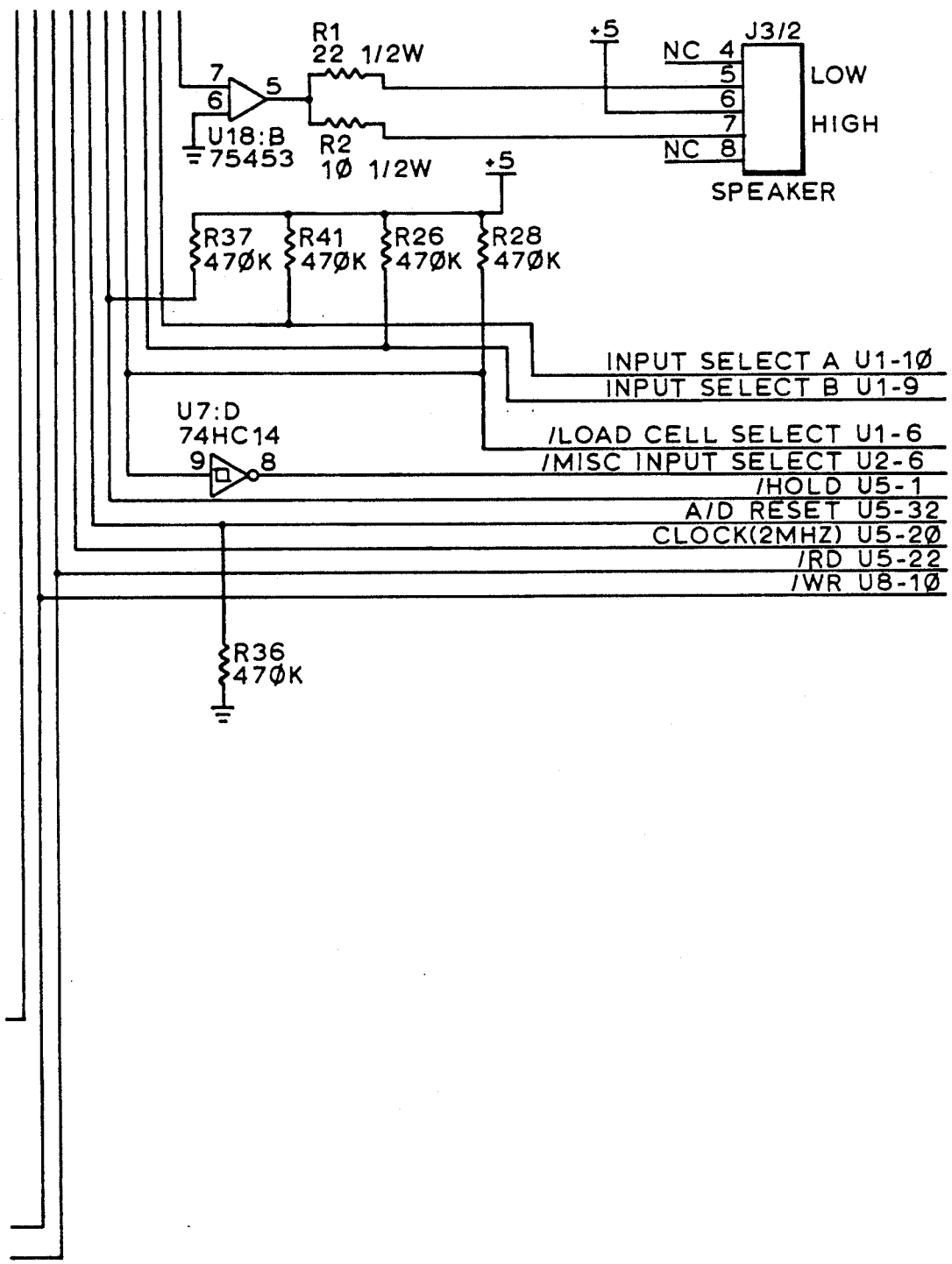
Figure 7:
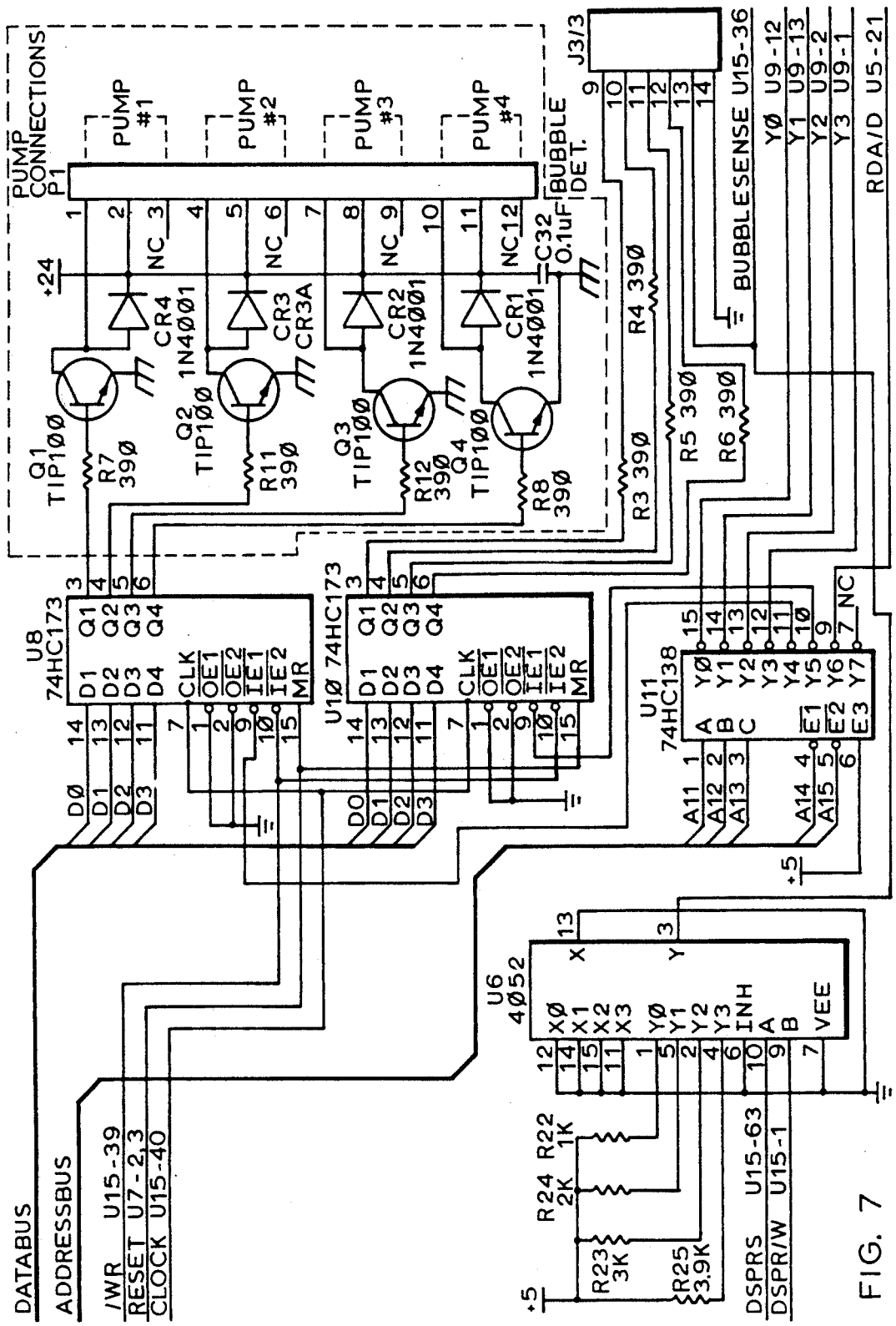
FIG. 7 is a schematic diagram of a portion of the electronic circuitry of the fluid compounding apparatus of FIG. 1.

FIGS. 5 through 7 depict the actual schematic diagrams for the apparatus 20, from which the block diagram of FIG. 4 was derived. A detailed description of the schematic circuitry of FIGS. 5 through 7 is deemed unnecessary to an understanding of the invention inasmuch as the schematics show the actual circuitry employed In the preferred embodiment of the apparatus 20, and such schematics show components with values and manufacturer's nomenclature, with component pin designations and nomenclature set forth in accordance with standard electronic schematic drafting practices.

For example, the integrated circuit components are designated by the letter "U" followed by a component number, such as "U1" and "U2" in FIG. 5, both of which are identified by manufacturer's designation "4052B", these particular components being the "multiplexer" collectively designated by reference numeral 110 in the block diagram of FIG. 4. Within the components U1 and U2, there are designated various signals associated with a multiplexer, e.g., X0, X1, etc., and outside the block for U1 and U2, there are a plurality of arabic numerals (1 through 16) which are the "pin designations", this being a 16-pin packaged IC (integrated circuit) component. Similarly, on the right side of FIG. 5, there is an enlarged block designated "U5", with manufacturer's designation CS5014KC28, this component being the analog to digital converter 114 shown in FIG. 4.

The component blocks designated "J1/1", "J1/2", "J2/1", and "J2/2" are jacks or connectors for connection to the four load cells 26 (not shown in FIG. 5), while the block "J3/1" is the connector for the temperature sensor 69 (not shown in FIG. 5). FIG. 5 basically depicts the circuitry for multiplexing of the analog load cell and temperature signals, which are then converted to digital values through component U5, that is A/D converter 114. Input and output lines are shown adjacent the opposite edges of FIG. 5, such as "load cell select" adjacent the left margin, followed by the term "U15-15". The first part of the designation defines the input or output control signal, with the latter part of the designation denoting the signal is received from pin 15 of component U15, which, as shown in FIG. 6, is the large block in the upper center of the diagram designated by manufacturer's designation M58734, this being a Mitsubishi microprocessor utilizing an expanded 6052 instruction set. The microprocessor includes internal ROM (read-only memory) into which the program is loaded for operation of the system.

In FIG. 5, the circuitry is divided with a vertical broken line, passing through component U5, which is designated at the top thereof with the words "analog" to the left of the line and "digital" to the right of the line, with a bold line at the upper right designated "data bus D0–D7" showing the digital data output of the A/D converter.

FIGS. 6 and 7 will be discussed briefly to correlate parts thereof with the block diagram of FIG. 4. In the upper left of FIG. 6, the block designated "J6" shows "To K/BD", which indicates that this is the connector to the keyboard control panel 21, with block designated "J8" therebelow being the connector to the "barcode reader" or wand 70. The connectors on the right side include connector "J7" which provide electrical connection to the display 80. Connector "J4" is designated "RS-232 PORT", which provides communication with a personal computer, if desired. Below that is connector "J3/2" which is for connection to a speaker for providing audible alarm signals to the operator.

The circuitry of FIG. 7 addresses two basic functions, these being the flow sensing via the "bubble detectors" connected to connector "J3/3" at the bottom right, and the pump controller 130 of FIG. 4, enclosed in the dotted rectangle at the upper right of FIG. 7. A vertical block strip within the dotted lines is designated "Pump Connections" indicating a contact strip for connection to the pumping devices 57–60, described as "pump #1", "pump #2", etc. within the dotted line rectangle.

In all three figures, interconnection to the leads or buses of others of the three figures are clearly designated by nomenclature on the terminating lead identifying the source or destination or function, along with the component and pin number to which it is connected, those of ordinary skill in the art may readily understand the circuitry of FIGS. 5 through 7 without a detailed description thereof.

Overview of the Program

In accordance with the invention, the ROM of the microprocessor controller 100 includes a software program for performing the control of the pumping. The software is divided into two basic sections: The main operating program and its associated sub-functions and the interrupt system. The main program processes key functions, error checking & processing, pump logic, print formatting, bubble processing, and other such higher level, slow, or non-realtime events. The interrupt system processes all timed events and passes results to the main program for further action. These include load cell sampling & filtering, bubble detector sampling & filtering, timers, barcode reader input, audio output, pump duty cycle control, keyboard scanning, and serial port input.

The overall main flow of the program includes the following steps:
(1) Start up, initialize hardware, check system, enable interrupts
(2) Infinite loop:
  (a) Process any pending keys; vector to appropriate function
  (b) Output any pending serial output data
  (c) Check load cells for error condition every 640 ms.
  (d) If flashing, re-write appropriate display sections
  (e) If pumping, check current volumes for finish. At end, recheck stable volumes & format print output
  (f) If enabled, check for bubble stop or pumping timeout failure
  (g) Loop to top.

Within the program, the following steps are involved in the interrupt structures:
(1) 2.5 ms Timer
(2) Read and average next load cell (1 of 4)
(3) Select next load cell for next cycle
(4) Read next bubble detector and perform filtering
(5) Select next bubble detector for next cycle
(6) Process various timers, set flags for main as required
(7) If pumping, turn on all enabled pumps and restart duty cycle timers (every 10 ms)
(8) Scan for keys every 20 ms.
(9) Exit The sequence for pump actuation is as follows:
(1) Pump Motor Duty Cycle Timer
(2) Processed 1.3, 1.5, 2.0, 3.0, and 8.5 ms after above 10 ms pump start
(3) Turn off pumps running at this duty cycle
(4) Exit The sequence for use of the wand 70, that is the barcode reader is as follows:
(1) Barcode reader
(2) Capture time that edge occured > save in buffer
(3) Reverse edge polarity and restart timer
(4) When XX bits have arrived, start timeout timer; time values processed at end of timeout (100 ms)
(5) Exit The following illustrate selected program examples and are more detailed "code" and comments of the main loop, the pump update logic and the start key processing. The syntax is "C" language syntax, and some of the code has been deleted for more clarity.

Main program

The following is the main program for the system:
* Start up:
  * Verify ROM & RAM. If error, display message and halt system.
  * Initialize various flags and values.
  * Select load cell input & turn on timerx interrupts.
  * If this is a cold start, do cold start initializations, then
  * set flag
  * Check Calibration variables for validity.
  * Check setup memory. If error, reinitialize the setup memory.

The above program, values, definitions and functions assist in an understanding of the programs hereinabove set forth. By way of example, as previously described, in accordance with the invention, to provide accuracy, the varying lengths of the tubing 47–50 is taken into consideration by the defined fixed tubing offsets per tubing leg, by the defined terms "OFFSET_0" being 19.0 ml for the first pumping device 57; the term "OFFSET_1" being 17.5 ml for the pumping device 58; the term "OFFSET_2" being 16.0 ml for the pumping device 59; and the term "OFFSET_3" being 14.5 ml for the pumping device 60.

The assigned terms and values for the keyboard of the control panel 21 are set forth in the key definition section hereinabove as "KEY_0" is "0", "KEY_1" is "1", . . . "KEY_9" is "9", "KEY_VOL" is "V", "KEY_SPG" is "G", etc., the key definitions corresponding to the keys available at the control panel 21.

The "calibrate" key enables initial calibration of the system by utilization of a known precise weight, such as 1000 grams. During pumping, as hereinabove described, the pump seeds are varied in accordance with the stage of pumping, between high, medium and low speeds, as above defined, with "jogging" of the pump taking place during the final pumping stage just prior to topping off the solution, this determination being made based on a calculated time to completion of the dispensed solution. For this purpose, an averaging is utilized, the program for which gets an average over 5 "lcavg" (load cell average) cycles, this being 128 load cell samples. The program sets "longavg" in "asmdata" to the new averaged value, the time for which takes at least 1.36 seconds or "pumpcnt" time whichever is longer.

| Load Cell Averaging Program |
|---|
| ```
*/
{
register char i;                    /* register pointers */
register struct idata *q;
register struct pdata *p;
register char n;
register int delta;
register boolean wasunsteady;
strcpyblk(savecenter, dspcenter, sizeof(dspcenter));  /* save
    screen image */
if (pumpcnt > 190)
    CntrPutS("Please wait.. nVolume check", 0); /* only print
        wait msg on long wait */
again:
InitErrChk( );                      /* init error checking cells */
wasunsteady = FALSE;
while (pumpcnt > 128)               /* wait - settling time if any */
    sout( );
asmdata[0].avrscnt = AVG_RES;       /* restart averages (load
                                       cells & temp/eos */
asmdata[1].avrscnt = AVG_RES;
asmdata[2].avrscnt = AVG_RES;
asmdata[3].avrscnt = AVG_RES;
asmdata[0].longavg = 0;
asmdata[1].longavg = 0;
asmdata[2].longavg = 0;
asmdata[3].longavg = 0;
for (n = 0; n < 4; n++)             /* loop to sum 4 lcavg samples */
{
if (!syringe || n < 2)              /* syringe mode uses only two actual
                                       readings */
    {
    pumpcnt = AVG_TIME;
    while (pumpcnt)
        sout( );
    }
for (loopsetup( ); i < N_PUMPS; loopinc( ))
    q→longavg + =getint(&q→lcavg);
}
for (loopsetup( ); i < N_PUMPS; loopinc( ))
}
q→longavg = (q→longavg / 4);       /* divide result by 4 */
delta = iabs(q→longavg − q→oldavg);
/*
* Check for load cell reading out of tolerance with previous reading.
*/
``` |

| Load Cell Averaging Program |
|---|
| ```
if (delta > DELTA_CHECK)
    wasunsteady = TRUE;
}
if (wasunsteady)
{
CntrPutS("Don't disturb nsupply→key", 0);
error( );
WaitKey( );              /* wait for key, then restart weigh cycle */
pumpcnt = AVG_TIME;
while (pumpcnt)          /* wait briefly for settling */
    sout( );
pumpcnt = CAL_TIME;
goto again;
}
RestoreCntr( );          /* restore previous screen */
}
GetTempEos( )
/*
``` |

In accordance with the above, the system averages the load cell 26 readings by taking a first average of 128 cycles of load cell readings. Then a further average is taken of the preceding four cycles of 128 readings, the averaging thus taking into consideration variations in fluid or solution flow occasioned by variables such as vibration, settling, tubing variations or the like.

This value provides a constant updating to the microprocessor 100 of the weight of each of the supply containers 37–40, which weight is then compared with the desired specific gravity adjusted weight entered by the operator for each solution to dispensed from the respective supply container. The "target volume" is thus monitored against the "new volume" so computed to determine the "volume to go" (i.e., the volume remaining to be pumped). This "volume to go" value, in turn, determines the pumping speed, from an initial "high" value through a "medium" to a "low" value, and then "jogging" to obtain the final desired fluid or solution amount.

The construction of the apparatus 20 is such, physically, that the supply containers 37–40 rest in cradles 27–30 positioned as low as physically possible to avoid undue vibration which would impact on load cell measurements, and thus require less "settling" time between measurements.

While there has been shown and described a preferred embodiment, it is to be understood that various other adaptations and modifications may be made within the spirit and scope of the invention.

What is claimed is:

1. A fluid compounding apparatus for pumping solutions from a plurality of supply containers into a receiving container, said apparatus comprising:
   a plurality of pumping means;
   a like plurality of supply container receiving stations, each of said stations including means for supporting a supply container and a weight sensing means cooperatively coupled to said supporting means for sensing the weight of the supply container and the solution therein;
   manifold means;
   tubing means for connection from each supply container to said manifold means and for connecting said manifold means to a receiving container configured for receiving therein solution from the supply containers;
   control means for enabling operation of said pumping means;

means for enabling the input of information into said control means of the amount of solution to be dispensed from the solution in each of the dispensing containers; and means within said control means responsive to the input of said information for enabling generally simultaneous commencement of operation of each of said plurality of pumping means and for enabling selective cessation of each of said pumping means in response to said input information for enabling pumping of the solution from each one of the dispensing containers of an amount of solution determined in accordance with the input information for the particular pumping station.

2. The combination according to claim 1 wherein said means for supporting the supply containers includes cradle means in spaced relation on a housing means.

3. The combination according to claim 2 wherein said manifold means are positioned adjacent a side of said housing means and said tubing means includes tubing from each supply container to said manifold means, and wherein at least some of said lengths of tubing vary in length.

4. The combination according to claim 3 wherein said control means includes means for taking into account variables associated with any solution in each of said lengths of tubing.

5. The combination according to claim 1 wherein said means for enabling the input of information into said control means include means for inputting the desired volume of each solution at each pumping station and means for inputting the specific gravity of each such solution.

6. The combination according to claim 5 wherein said means within said control means responsive to the input of said information includes means for converting the desired volume and specific gravity of each solution into a weight factor which is compared against the weight of said sensing means.

7. The combination according to claim 6 wherein said sensing means includes load cells.

8. The combination according to claim 6 wherein said means within said control means responsive to the input of said information includes means for averaging samples from said weight sensing means to determine a long term average weight as a basis of comparison against said weight factor.

9. The combination according to claim 1 wherein said pumping means includes peristaltic pumping devices and wherein said tubing means includes lengths of tubing, each individual length of tubing at each pumping station passing from a supply container through said peristaltic pump to said manifold means.

10. The combination according to claim 9 wherein said apparatus further includes means in optical relation with each of said lengths of tubing for sensing fluid flow therethrough.

11. A fluid compounding apparatus for pumping solutions from a plurality of supply containers into a receiving container, said apparatus comprising:

base housing means configured for support on a surface;

subhousing means attached to the upper surface of said base housing means;

a plurality of supply container receiving stations, each of said stations including cradle means on said subhousing means and weight sensing means within said subhousing means with means interconnecting said cradle means and said weight sensing means, each of said cradle means being configured for supporting a supply container with the discharge end thereof facing downwardly, said weight sensing means sensing the weight of the supply container and the solution therein;

a like plurality of pumping means within said housing means, said subhousing means and each of said pumping means including means for passage of tubing from the discharge ends of each of the supply containers through said pumping means to a receiving container;

control panel means on said housing means for enabling the input of information into said control means of the amount of solution to be dispensed from the solution in each of the dispensing containers; and microprocessor means within said housing means responsive to the input of information via said control panel means for enabling generally simultaneous commencement of operation of each of said plurality of pumping means and for enabling selective cessation of each of said pumping means in response to said input information for enabling pumping of the solution from each one of the dispensing containers supported by said cradle means of an amount of solution determined in accordance with the input information for the particular pumping station.

12. The combination according to claim 11 further including manifold means and means for connecting said manifold means to each of the discharge ends of the supply containers and to a receiving container configured for receiving therein solution from the supply containers.

13. The combination according to claim 11 further including flow sensing means for determining the flow of fluid from the supply containers and means within said microprocessor means for affecting the operation of said pumping means in response to the output of said flow sensing means.

14. The apparatus according to claim 13 wherein said flow sensing means includes optoelectronic devices.

15. The apparatus according to claim 13 wherein said optoelectronic devices are configured and positioned for optically determining the flow of solution through the tubing of each supply container.

16. The combination according to claim 11 wherein said control panel means include means for inputting the desired volume of each solution at each pumping station and means for inputting the specific gravity of each such solution.

17. The apparatus according to claim 16 further including flow sensing means for determining the flow of fluid from the supply containers and means within said microprocessor means for affecting the operation of said pumping means in response to the output of said flow sensing means.

18. The combination according to claim 12 wherein said manifold means are positioned adjacent a side of said housing means and said means for connecting said manifold means to each of the discharge ends of the supply containers and to a receiving container includes tubing from each supply container to said manifold means, and wherein at least some of said lengths of tubing vary in length.

19. The combination according to claim 18, wherein said control means includes means for taking into account variables associated with the volume of solution in each of said lengths of tubing.

20. A method for fluid compounding by pumping solutions from a plurality of supply containers by a like plurality of pump devices into a receiving container, said method comprising:

placing a plurality of supply containers on cradles having weight sensing means therebelow;

entering into a control means the amount of solution desired to be disposed from each of said supply containers;

generally simultaneously actuating the plurality of pump devices;

periodically sampling the weight of each of said plurality of supply containers;

sensing the flow of solution from each of said supply containers;

controlling the operation of each of said pump devices in accordance with the sampling of the weight of each of said supply containers compared with the amount of solution desired to be dispensed from each of said supply containers until the desired amount of each solution is dispensed; and interrupting the operation of all pump devices in the event the sensed flow of solution ceases.

21. The method according to claim 20 wherein said step of controlling the operation of each said pump devices includes controlling the speed of pumping.

22. The method according to claim 21 wherein the pumping of each solution is accomplished through lengths of tubing from each of said supply containers, and said method further includes offsetting the controlling of the pumps by a factor proportional to the amount of fluid in each individual length of tubing.

23. Fluid compounding apparatus for pumping solutions from a plurality of supply containers into a receiving container, said apparatus comprising:

base housing means configured for support on a surface;

subhousing means attached to the upper surface of said base housing means;

a plurality of supply container receiving stations, each of said stations including cradle means on said subhousing means and weight sensing means within said subhousing means with means interconnecting said cradle means and said weight sensing means, each of said cradle means being configured for supporting a supply container with the discharge end thereof facing downwardly, said weight sensing means sensing the weight of the supply container and the solution therein;

a like plurality of pumping means within said housing means;

manifold means;

tubing means including lengths of tubing interconnecting said manifold means and the discharge ends of each of the supply containers;

means for interconnecting said manifold means with a receiving container;

control panel means on said housing means for enabling the input of information into said control means of the amount of solution to be dispensed from the solution in each of the dispensing containers; and control means within said housing means responsive to the input of information via said control means for enabling generally simultaneous commencement of operation of each of said plurality of pumping means and for enabling selective cessation of each of said pumping means in response to said input information for enabling pumping of the solution from each one of the dispensing containers supported by said cradle means of an amount of solution determined in accordance with the input information for the particular pumping station.

24. The apparatus according to claim 23 further including means for sensing the flow of fluid through said lengths of tubing and for altering the response of said controlling means in accordance therewith.

25. The apparatus according to claim 24 wherein said flow sensing means includes optoelectronic devices configured and positioned for optically determining the flow of solution through the tubing of each supply container.

26. The apparatus according to claim 23 wherein said pumping means includes peristaltic pumps and wherein each individual length of tubing at each pumping station passes from a supply container through said peristaltic pump to said manifold means.

* * * * *